United States Patent [19]

Hopper et al.

[11] 4,350,818

[45] Sep. 21, 1982

[54] PREPARATION OF 2-(ISOPROPYLSULFINYL)BENZO-THIAZOLE

[75] Inventors: Roger J. Hopper, Akron; Budd H. Sturm, Hartville; Joseph F. Geiser, Akron, all of Ohio

[73] Assignee: The Goodyear Tire & Rubber Company, Akron, Ohio

[21] Appl. No.: 224,988

[22] Filed: Jan. 14, 1981

Related U.S. Application Data

[62] Division of Ser. No. 132,049, Mar. 20, 1980, Pat. No. 4,280,967.

[51] Int. Cl.$^3$ .................. C07D 277/76; C07D 277/74
[52] U.S. Cl. ..................................... 548/166; 548/165
[58] Field of Search ............................... 548/166, 165

[56] References Cited

U.S. PATENT DOCUMENTS

| | | | |
|---|---|---|---|
| 2,585,155 | 2/1952 | Mingasson | 548/166 |
| 2,910,480 | 10/1959 | Schneider | 548/165 |
| 2,912,357 | 11/1959 | Harman et al. | 548/165 |
| 3,454,590 | 7/1969 | Meale et al. | 548/166 |
| 3,985,762 | 10/1976 | Dransch et al. | 548/166 |

FOREIGN PATENT DOCUMENTS 118318  4/1944  Australia ............................ 548/165

OTHER PUBLICATIONS

Halasa et al., J. Org. Chem., 36, pp. 636–641 (1971).

Primary Examiner—David B. Springer
Attorney, Agent, or Firm—D. O. Nickey

[57] ABSTRACT

There is disclosed a novel class of vulcanization accelerators, specifically compounds such as 2-(isopropylsulfinyl)-benzothiazole.

1 Claim, No Drawings

PREPARATION OF 2-(ISOPROPYLSULFINYL)BENZOTHIAZOLE

This is a division, of application Ser. No. 132,049 filed Mar. 20, 1980; U.S. Pat. No. 4,280,967 issued July 28, 1981.

TECHNICAL FIELD

This invention relates to the sulfur vulcanization of rubber facilitated by a novel class of vulcanization accelerators. More particularly, the invention relates to rubbery compositions containing 2-(alkylsulfinyl)-benzothiazoles, to processes for vulcanizing such compositions, and to a process for synthesizing 2-(isopropylsulfinyl)-benzothiazole.

BACKGROUND ART

It is well-known in the rubber industry that preferred accelerators are those which, when mixed into vulcanizable rubber compositions and heated, exhibit an induction period (scorch delay) prior to the onset of vulcanization. It is also preferred that vulcanization proceed rapidly once the induction period has ended. Such a combination of characteristics has the practical benefits of maximum processing safety and shorter cure cycles. The present invention provides novel accelerator systems which meet these preferred criteria and also provides processes by which such preferred accelerator characteristics may be attained.

The sulfinyl benzothiazoles of the present invention may be prepared by adaptations of prior art procedures, wherein a 2-(alkylthio)-benzothiazole is first synthesized, then oxidized to its sulfinyl analog. The alkylthio benzothiazoles can be obtained by reaction of an alkali metal salt of 2-mercaptobenzothiazole with an alkyl halide as described in the following publications.

A. F. Halasa and G. E. P. Smith, Jr., *J. Org. Chem.*, 36 636 (1971).

C. G. Moore, *J. Chem. Soc.*, 4237 (1952).

W. A. Sexton, *J. Chem. Soc.*, 470 (1939).

V. F. Kucherov, *Zhur Obshchei Khim.*, 19, 752 (1949 *Chem. Abstr.*, 44, 3488f (1950).

Alternatively, 2-(alkylthio)-benzothiazoles have been prepared by reaction of an alkali metal alkyl mercaptide with 2-chlorobenzothiazole, c.f., P. E. Todesco and P. Vivarelli, *Boll. Sci. Fac. Chim. Ind. Bologna*, 20, 125 (1962), *Chem. Abstr.*, 59, 8562d (1963). The addition of 2-mercaptobenzothiazole to butene-1, butene-2, heptene-1 and heptene-3, catalyzed by $BF_3$ etherate, has been used to prepare the corresponding secondary alkylthio benzothiazoles, c.f., A. N. Bezumnova and N. K. Rozhkova, *Khim. Geterotsikl. Soedin.*, Sb., 1971, No. 3; *Chem. Abstr.* 78, 43342r (1973). This paper also discloses the preparation of 2-(tert.butylthio)-benzothiazole by reaction of 2-mercaptobenzothiazole with isobutylene in 80 percent sulfuric acid.

The Todesco et al. reference describes the preparation of 2-(methylsulfinyl)-benzothiazole by oxidation of the methylthio analog with peroxybenzoic acid. The preparations of 2-(alkylsulfinyl)-6-nitro-benzothiazoles by simultaneous oxidation/nitration with $HNO_3/H_2SO_4$ have been reported, c.f. *Ger. Offen.* No. 2,400,419 (7/17/75); *Chem. Abstr.*, 83, 179039h (1975).

In a report by A. E. Wood and E. G. Travis [*J. Am. Chem. Soc.*, 50, 1226 (1928)], a procedure is disclosed which uses aqueous sodium hypochlorite of "low alkalinity" to convert n-heptylsulfide to the sulfinyl analog in unspecified yield and purity. Other procedures are also known to be generally applicable for oxidation of thioethers to their sulfinyl analogs, c.f. S. R. Sandler and W. Karo, "*Organic Functional Group Preparations,*" Chapter 19, Academic Press, New York and London, 1968.

DISCLOSURE OF INVENTION

The present invention consists of a sulfur vulcanizable combination of a sulfur vulcanizable rubber and at least one compound having the general structural formula:

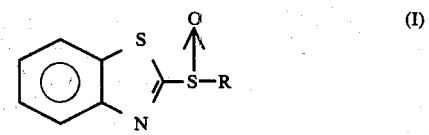

wherein R is selected from the group comprised of alkyl radicals of 1–20 carbon atoms, cycloalkyl radicals of 5–20 carbon atoms, or aralkyl radicals of 7–20 carbon atoms, and when R is alkyl or cycloalkyl, it may be substituted in the 2-position by a carboalkoxy radical.

Preferably R is an acyclic secondary alkyl radical of 3–12 carbon atoms, a cycloalkyl radical of 6–8 carbon atoms, or a tertiary alkyl radical of 4–12 carbon atoms.

Most preferably, R is an isopropyl radical. The following is a representative listing of the compounds of the present invention and are intended to be illustrative, but not limiting.

2-(isopropylsulfinyl)-benzothiazole
2-(sec-butylsulfinyl)-benzothiazole
2-(n-butylsulfinyl)-benzothiazole
2-(t-butylsulfinyl)-benzothiazole
2-(cyclohexylsulfinyl)-benzothiazole
2-(2'-carbomethoxyethylsulfinyl)-benzothiazole
2-(methylsulfinyl)-benzothiazole
2-(benzylsulfinyl)-benzothiazole
2-(2'-dodecylsulfinyl)-benzothiazole
2-(2'-tridecylsulfinyl)-benzothiazole
2-(2',4',4'-trimethyl-2'-pentylsulfinyl)-benzothiazole The accelerators of this invention may be incorporated into rubber along with other conventional ingredients, by standard mixing techniques. While the amount used depends on the specific formulation, and on the vulcanization characteristics and vulcanizate properties desired, a range of 0.1–10 parts per hundred parts of rubber is generally effective. A range of 0.4–3.0 parts per hundred parts of rubber is preferred.

The sulfinyl benzothiazoles of the present invention can be used with any sulfur vulcanizable rubber including natural and synthetic rubbers and mixtures thereof. Synthetic rubbers include homopolymers and copolymers of dienes, both conjugated and nonconjugated, e.g., 1,3-dienes such as 1,3-butadiene and isoprene. Examples of such synthetic rubbers include neoprene (polychloroprene), cis-1,4-polybutadiene, cis-1,4-polyisoprene, butyl rubber and copolymers of 1,3-butadiene or isoprene with monomers such as styrene, acrylonitrile, isobutylene and methyl methacrylate. The accelerators of this invention can also be used with ethylene-propylene terpolymers (EPDM) as well as polypentenamers derived from ring opening polymerization of cyclopentene.

Conventional additives suitable for use in conjunction with the accelerators of the present invention include fillers (e.g. carbon black and silica), metal oxides (e.g. zinc oxide), fatty acids (e.g. stearic acid), phenolic or amine-based antidegradants, and elemental sulfur or an organic sulfur donor (e.g. amine disulfides, alkylphenol disulfides, and polymeric polysulfides).

The sulfinyl-benzothiazoles may be used as the sole accelerator, but are preferably used in combination with other accelerators. When used with conventional delayed action accelerators (e.g. benzothiazole sulfenamides, aminodithiobenzothiazoles, thiocarbamyl sulfenamides), the sulfinyl benzothiazoles serve as secondary accelerators or activators, increasing the state of cure and rate of cure with minimal adverse effects on the induction period prior to vulcanization. More preferably, however, the sulfinyl benzothiazoles are used as primary accelerators in the presence of smaller amounts of secondary accelerators or activators. Suitable activators include tetra-alkylthiuram disulfides, tetra-alkylthiuram monosulfides, diaryl guanidines, aldehyde-amine condensation products, and organophosphorous sulfides (e.g. O,O'-diisopropylthiophosphoryl-di(and tri-)sulfide).

With stocks accelerated by the sulfinyl benzothiazole-activator systems the induction period prior to vulcanization may, if desired, be increased by addition of retarders such as S,S-di(isopropyl)-N-(p-toluene sulfonyl)sulfilimine or N-cyclohexylthiophthalimide.

The effects of the accelerators of this invention in vulcanizable rubber compounds were evaluated by the following procedures. Mooney Scorch tests were performed using the large or small rotor as described in ASTM D1646-61, continuously recording viscosity versus time. The number of minutes, t$\Delta$5 or t$\Delta$3, required for the viscosity curve to rise five (large rotor) or three (small rotor) points above the minimum was taken as a measure of the induction period prior to vulcanization (i.e. scorch inhibition). Larger values for t$\Delta$5 or t$\Delta$3 indicate greater resistance to scorch or premature vulcanization.

Cure characteristics were determined on an oscillating disk rheometer, essentially according to ASTM D-2084-71-T (3° arc, 1.67 Hz.) Pertinent data reported are: $t_4$, the time to a 4 in. lb (0.45 N.m) rise above the minimum; $\Delta$Torque, the maximum torque after curing minus the minimum torque; $t_{90}$, the time required to reach 90% of full torque development. Stocks with longer $t_4$'s in combination with shorter $t_{90}$'s are preferable, being indicative of better prevulcanization resistance followed by shorter cure time. The value, $\Delta$Torque, is taken as a measure of the relative state of cure, while $t_{90}$ is considered to approximate the optimum cure time.

Tensile strength, elongation, and stress at 300 percent elongation were obtained according to standard procedures wherein dumbbell samples were cut from vulcanized sheets and tested in a conventional tensile tester. Values reported are: U.T.S., the ultimate tensile strength; U.E. the ultimate elongation; 300 percent M, the stress at 300 percent elongation.

Examples of accelerators within the scope of this invention along with melting points are listed in Table I.

TABLE I

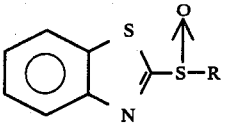
(I)

2-(Alkylsulfinyl)-Benzothiazoles

| Accelerator | R | mp., °C. |
|---|---|---|
| A | isopropyl | 87–88.5 |
| B | n-butyl | liquid (room temp.) |
| C | sec-butyl | 58–67 |
| D | tert-butyl | 84.5–86 |
| E | benzyl | 120–121.5 |
| F | 2-carbomethoxy-ethyl | 113–114.5 |
| G | cyclohexyl | 109.5–111 |
| H | methyl | 71–72.5 |

With the exception of accelerator H, all compounds in Table I apparently represent novel chemical compositions not reported or suggested in the prior art. These new compositions were characterized by proton magnetic resonance and infra red spectroscopic techniques and, with the exception of C, by elemental analyses which showed the (theoretical±0.4) percentages for carbon, hydrogen, nitrogen and sulfur. Liquid chromatography analysis combined with proton magnetic resonance analysis of accelerator C indicated a mixture of two diasteromers.

More Detailed Description of the Disclosure

A preferred compound of this invention, 2-(isopropylsulfinyl)-benzothiazole was prepared by a novel process. First, 2-(isopropylthio)-benzothiazole was synthesized by reaction of 2-mercaptobenzothiazole with propylene in the presence of a monomeric or polymeric arenesulfonic acid catalyst. While the process is similar to that of the cited Bezumnova and Rozhkova reference, the use of a sulfonic acid catalyst represents an improvement in that the corrosion problems associated with BF$_3$ etherate are avoided. In the second step, the 2-(isopropylthio)-benzothiazole was oxidized to 2-(isopropylsulfinyl)-benzothiazole with aqueous sodium hypochlorite under conditions of high frequency mechanical homogenization. For satisfactory results, the reaction required NaHSO$_4$ or KHSO$_4$ to generate an acidic medium and urea to suppress overoxidation to 2-(isopropylsulfonyl)-benzothiazole. The acidic medium is in contrast to the alkaline conditions of Wood and Travis cited above. The beneficial effect of small amounts of urea was surprising and unanticipated. The exact role of urea is in the process of this invention not clearly understood.

BEST MODE FOR CARRYING OUT THE INVENTION

The following examples are intended to illustrate processes for preparation of the preferred compound and not to limit the scope of the present invention.

EXAMPLE 1

To prepare 2-(isopropylthio)-benzothiazole, a one liter autoclave fitted with a stirrer, thermocouple, pressure gage, and gas vent was charged with 167 grams of 2-mercaptobenzothiazole, 350 ml. of xylene, 30 grams of Amberlyst-15 ® (Trademark for Rohm & Haas' sulfonated styrene-divinylbenzene resin), 128 grams of propylene, and sealed. The reaction mixture was heated to 150° C. for five hours with stirring. The pressure in the vessel rose to 480 psig and then decreased to 244 psig. After cooling and venting the reactor, the reaction mixture was filtered to remove the Amberlyst-15 ® and the resulting solution analyzed by gas chromatography to determine that 191 grams of 2-(isopropylthio)-benzothiazole was present (91% yield). Xylene was removed by steam distillation, leaving oily product suitable for direct use as the starting material for 2-(isopropylsulfinyl)-benzothiazole. Alternatively, the oily product may be vacuum distilled to obtain a more highly purified material with a boiling point of 107°–114° C. at 0.46–0.65 mm. of Hg.

EXAMPLE 2

The process of Example 1 was carried out with 5 grams of p-toluenesulfonic acid in place of Amberlyst-15 ®. After 3.5 hours at 200° C. an 83% yield of 2-(isopropylthio)-benzothiazole was obtained.

EXAMPLE 3

The process of Example 1 was carried out in the absence of a sulfonic acid catalyst. After 4 hours at 237° C., only a 66% yield of 2-(isopropylthio)-benzothiazole was obtained. In contrast to Examples 1 and 2, the product was contaminated with high boiling impurities.

EXAMPLE 4

To prepare 2-(isopropylsulfinyl)-benzothiazole, a cylindrical glass vessel, 9 cm. in diameter×15 cm. high was charged with 40.0 g. of distilled 2-(isopropylthio)-benzothiazole, 200 ml. of $H_2O$, and 308 ml. of sodium hypochlorite (0.778 M NaOCl, 0.605 grams excess NaOH/liter). After fitting the reactor with a thermometer and pH electrode, the two phase mixture was homogenized with a Tekmar Model SD-45N mechanical high frequency homogenizer equipped with a G-456 generator head, and operated at 7,000–9,000 rpm. The mixture, with pH>10, was cooled to 15° C. and a solution of 4 grams $NaHSO_4.H_2O$ and 2 grams urea in 20 ml. of $H_2O$ rapidly added. Within less than 30 seconds, the temperature rose to 35° C., the pH dropped to 2.0 and a white solid precipitated. After 5 minutes of subsequent homogenization, 1 gram of $Na_2SO_3$ was added to decompose excess NaOCl, and the pH adjusted to 7.0±0.5 by addition of $Na_2CO_3$. The reaction slurry was then cooled to 25° C., filtered, and the solids washed with water, filtered and dried at 40° C. The yield was 40.7 g. (95% of theory) with a melting point of 83.5°–87° C.

High pressure liquid chromatographic analysis showed the product to contain 97 weight percent 2-(isopropylsulfinyl)-benzothiazole and 2 weight percent 2-(isopropylsulfonyl)-benzothiazole. An analytically pure sample (Table I, Accelerator A) is obtained by washing with petroleum ether followed by recrystallization from 2-propanol.

EXAMPLE 5

The process of Example 4 was carried out using 4 gm $KHSO_4$ instead of $NaHSO_4.H_2O$, and subsequently homogenizing for 30 minutes. The final pH was 1.9. The product, 94% of theory, contained 97 weight percent 2-(isopropylsulfinyl)-benzothiazole and 3 weight percent 2-(isopropylsulfonyl)-benzothiazole and melted at 82°–86° C.

EXAMPLE 6

The process of Example 5 was repeated in the absence of urea. The product, 93% of theory, contained 83 weight percent 2-(isopropylsulfinyl)-benzothiazole and 11 weight percent 2-(isopropylsulfonyl)-benzothiazole, the remainder being primarily unreacted starting material. The melting point was 71°–80° C.

EXAMPLE 7

A process similar to Example 5 was carried out, but with only 20 percent of the relative amount of $KHSO_4$, and produced a final pH of 6.5. The product was a semi-solid paste.

The following Tables are intended to illustrate the uses of the accelerators of this invention in various rubber formulations. Table II lists the basic recipes used in the subsequent Tables. Well-known commercially available compounding ingredients appearing in the Tables are abbreviated as follows: MDB, 2-(4-morpholinodithio) benzothiazole; MBS, 2-(4-morpholinothio)benzothiazole; DBM, 4,4'-dithiobis(morpholine); CBS, N-cyclohexyl-2-benzothiazole sulfenamide; DPG, diphenyl guanidine; BBTS, N-(t-butyl)-2-benzothiazole sulfenamide; TMTD, tetramethylthiuram disulfide; TMTM, tetramethylthiuram monosulfide; MBTS, 2,2'-dithiobis(benzothiazole); RES, resorcinol; HMTA, hexamethylene tetramine; CTP, N-cyclohexylthiophthalimide. Other abbreviations are as follows: IPS, S,S-di(isopropyl)-N-(p-toluenesulfonyl) sulfilimine; DITS, O,O'-diisopropylthiophosphoryl disulfide. Wingstay ®100 is a diaryl-p-phenylene diamine antioxidant. Wingstay ®300 is an alkyl, aryl-p-phenylene diamine antiozonant. The amount of components shown in the Tables are parts by weight. Within each of Tables III–V are more than one test series. Each individual series, with its own controls, is characterized by a different letter prefix for the test stock number.

In Table III, Stocks A-1 through A-4, B-1 and B-2, and D-1 through D-4 show the use of the sulfinyl benzothiazoles as activators for natural rubber formulations containing typical delayed action accelerators (i.e. MDB, MBS, CBS, BBTS). In general, the sulfinyl benzothiazoles cause a reduction in cure time ($t_{90}$), an increase in the modulus or state of cure (Torque, 300% M), and a small to moderate decrease in scorch inhibition ($t_4$, $t\Delta 5$). Stock A-5 illustrates the use of accelerators of this invention with DBM to provide cure characteristics similar to the MDB system (Stock A-1). Stock B-3 shows that Accelerator A, activated by DPG, produces cures comparable to CBS (Stock B-1). The well-known additive combination, RES/HMTA, activates Accelerator A to give a cure comparable to BBTS (Stock C-2 versus Stock C-1).

Sulfinyl benzothiazole/activator systems in natural rubber are illustrated in Table IV. Stocks E-5 and E-8 through E-11 versus E-1 show that sulfinylbenzothiazole/TMTM systems produce about the same vulcanizate properties as MBD, but have the advantage of substantially shorter cure times ($t_{90}$). These stocks also illustrate that the scorch inhibition ($t_4$, $t\Delta 5$) varies with the nature of the alkyl group on the sulfinyl benzothiazole. Stocks E-2 through E-4 are included to show that the cure characteristics of E-5 cannot be achieved by equivalent activation of MDB with TMTM, or by the accelerator or activator components individually. Stock E-5 is also illustrative of the long cure times usually characteristic of the sulfinyl benzothiazoles in the absence of activators. Stocks F-2 through F-4 compare additional examples of sulfinyl benzothiazole/TMTM systems with MDB (Stock F-1). The accelerator/activator combination of Stock F-5 is essentially equivalent to MDB (Stock F-1), and is of use in applications where a formulation free of amine residues is desired (e.g. in rubber adjacent to fabrics which may be degraded by amines).

The use of a preferred sulfinyl benzothiazole (Accelerator A) as a primary accelerator in a typical synthetic rubber tread stock is shown in Table V. For comparison, Stocks G-1 through G-4 and H-1, are representative of present state-of-the-art recipes employing delayed action accelerators. Stock G-5 typifies older industrial formulations having marginal processing safety by current standards. It can be seen from Stocks G-6 and G-7 and H-2 through H-4 that Accelerator A, in combination with appropriate activators (e.g. DPG, TMTD, TMTM) produces cure characteristics and vulcanizate properties comparable to those preferred in the rubber industry.

TABLE II

| Component | Base Stock | |
|---|---|---|
| | NR | OESBR/BR |
| Natural Rubber | 100.0 | |
| SBR-1712 | | 103.0 |
| High-cis-Polybutadiene | | 25.0 |
| HAF Carbon Black | 50.0 | |
| ISAF Carbon Black | | 68.0 |
| Highly Aromatic Oil | | 10.0 |
| Hydrocarbon Softener | 3.0 | |
| Zinc Oxide | 3.0 | 3.5 |
| Stearic Acid | 3.0 | 2.0 |
| Wingstay ® 100 | 1.0 | 1.0 |
| Wingstay ® 300 | | 1.5 |
| Sulfur | 2.5 | 1.8 |

TABLE III

| | Test Stock | | | | | | | | | | | | | |
|---|---|---|---|---|---|---|---|---|---|---|---|---|---|---|
| | A-1 | A-2 | A-3 | A-4 | A-5 | B-1 | B-2 | B-3 | C-1 | C-2 | D-1 | D-2 | D-3 | D-4 |
| Part 1 | | | | | | | | | | | | | | |
| Component | | | | | | | | | | | | | | |
| NR Base Stock | 162.5 | → | → | → | → | → | → | → | → | → | → | → | → | → |
| MDB | 0.50 | 0.50 | | | | | | | | | 0.50 | 0.50 | 0.50 | 0.50 |
| MBS | | | 0.50 | 0.50 | | | | | | | | | | |
| CBS | | | | | | 0.50 | 0.50 | | | | | | | |
| BBTS | | | | | | | | | 0.50 | | | | | |
| DPG | | | | | | | | 0.30 | | | | | | |
| DBM | | | | | 0.40 | | | | | | | | | |
| RES | | | | | | | | | 1.0 | 1.0 | | | | |
| HMTA | | | | | | | | | 1.0 | 1.0 | | | | |
| Accelerator A | | 0.50 | | 0.50 | 0.40 | | 0.50 | 0.50 | | 0.50 | 0.50 | | | |
| Accelerator C | | | | | | | | | | | | | 0.53 | |
| Accelerator F | | | | | | | | | | | | | | 0.56 |
| Part 2 | | | | | | | | | | | | | | |
| Test | | | | | | | | | | | | | | |
| Rheometer (135° C.) | | | | | | | | | | | | | | |
| $t_4$, minutes | 12.5 | 13.3 | 13.0 | 13.5 | 14.9 | 12.1 | 11.7 | 12.1 | 11.8 | 11.3 | 15.3 | 14.3 | 14.0 | 12.8 |
| $t_{90}$, minutes | 46.0 | 39.0 | 43.0 | 34.5 | 45.0 | 46.0 | 34.0 | 45.0 | 49.2 | 46.0 | 54.0 | 45.5 | 44.2 | 44.2 |
| ΔTorque, N.m | 6.35 | 7.05 | 6.45 | 6.94 | 7.06 | 5.80 | 6.37 | 6.23 | 8.23 | 7.56 | 6.32 | 6.64 | 6.63 | 6.39 |
| Mooney Scorch (120° C.) | | | | | | | | | | | | | | |
| $t\Delta 5$, minutes | | | | | | 19.7 | 18.7 | 20.5 | 18.2 | 18.2 | 26.8 | 20.8 | 20.2 | 16.8 |
| Stress-Strain, cured | | | | | | | | | | | | | | |
| $t_{90}$ minutes at 135° C. | | | | | | | | | | | | | | |
| U.T.S. MPa | | | | | | | | | 26.1 | 26.3 | 27.3 | 27.1 | 26.6 | 26.4 |
| U.E., % | | | | | | | | | 455 | 460 | 540 | 495 | 495 | 520 |
| 300% M, MPa | | | | | | | | | 17.6 | 17.0 | 14.0 | 15.4 | 15.1 | 14.8 |

TABLE IV

| | Test Stock | | | | | | | | | | | | | | | |
|---|---|---|---|---|---|---|---|---|---|---|---|---|---|---|---|---|
| | E-1 | E-2 | E-3 | E-4 | E-5 | E-6 | E-7 | E-8 | E-9 | E-10 | E-11 | F-1 | F-2 | F-3 | F-4 | F-5 |
| Part 1 | | | | | | | | | | | | | | | | |
| Component | | | | | | | | | | | | | | | | |
| NR Base Stock | 162.5 | → | → | → | → | → | → | → | → | → | → | → | → | → | → | → |
| MDB | 0.50 | 0.50 | | | | | | | | | | 0.50 | | | | |
| TMTM | | 0.10 | 0.10 | | 0.10 | → | → | → | → | → | → | | 0.10 | → | → | |
| IPS | | | | | | 0.20 | | | | | | | | | | |
| CTP | | | | | | | 0.20 | | | | | | | | | |
| DITS | | | | | | | | | | | | | | | | 0.20 |
| Accelerator A | | | | 0.50 | → | → | → | | | | | | | | | 0.50 |
| Accelerator B | | | | | | | | 0.53 | | | | | | | | |
| Accelerator C | | | | | | | | | | 0.53 | | | | | | |
| Accelerator D | | | | | | | | | | | | | | | 0.53 | |
| Accelerator E | | | | | | | | | | | | 0.61 | | | | |
| Accelerator F | | | | | | | | | | | 0.56 | | | | | |
| Accelerator G | | | | | | | | | 0.59 | | | | | | | |
| Accelerator H | | | | | | | | | | | | | | 0.44 | | |
| Part 2 | | | | | | | | | | | | | | | | |
| Test | | | | | | | | | | | | | | | | |
| Rheometer (135° C.) | | | | | | | | | | | | | | | | |
| $t_4$, minutes | 15.1 | 11.0 | 12.6 | 17.8 | 15.9 | 17.8 | 17.6 | 14.0 | 13.2 | 12.8 | 16.0 | 12.3 | 12.0 | 12.8 | 9.9 | 14.8 |

TABLE IV-continued

|  | Test Stock | | | | | | | | | | | | | | | |
|---|---|---|---|---|---|---|---|---|---|---|---|---|---|---|---|---|
|  | E-1 | E-2 | E-3 | E-4 | E-5 | E-6 | E-7 | E-8 | E-9 | E-10 | E-11 | F-1 | F-2 | F-3 | F-4 | F-5 |
| $t_{90}$, minutes | 55.5 | 24.0 | 41.5 | 77.5 | 35.0 | 40.0 | 39.0 | 37.5 | 38.0 | 28.8 | 34.3 | 50.5 | 32.0 | 34.7 | 23.3 | 51.3 |
| Torque, N.m | 5.73 | 8.88 | 4.63 | 5.74 | 6.59 | 6.70 | 6.68 | 6.27 | 6.50 | 6.52 | 6.62 | 6.62 | 6.52 | 6.52 | 6.73 | 6.28 |
| Mooney Scorch (121° C.) | | | | | | | | | | | | | | | | |
| $t\Delta 5$, minutes | 23.4 | 15.2 | 16.6 | 24.0 | 20.6 | 25.4 | 24.2 | 19.6 | 18.3 | 16.1 | 22.5 | — | — | — | — | — |
| Stress-Strain, cured | | | | | | | | | | | | | | | | |
| $t_{90}$ minutes at 135° C. | | | | | | | | | | | | | | | | |
| U.T.S., MPa | 25.8 | 25.0 | 24.9 | 26.6 | 25.2 | 26.6 | 25.3 | 25.0 | 26.4 | 26.3 | 27.0 | — | — | — | — | — |
| U.E., % | 525 | 420 | 630 | 580 | 525 | 560 | 515 | 525 | 550 | 555 | 555 | — | — | — | — | — |
| 300% M, MPa | 13.3 | 17.9 | 9.3 | 12.2 | 13.1 | 13.1 | 12.9 | 12.0 | 12.9 | 13.0 | 13.1 | — | — | — | — | — |

TABLE V

|  | Test Stock | | | | | | | | | | |
|---|---|---|---|---|---|---|---|---|---|---|---|
|  | G-1 | G-2 | G-3 | G-4 | G-5 | G-6 | G-7 | H-1 | H-2 | H-3 | H-4 |
| Part 1 | | | | | | | | | | | |
| Component | | | | | | | | | | | |
| OESBR/BR Base Stock | 215.8 | → | → | → | → | → | → | → | → | → | → |
| MDB | | | | | | | | 1.1 | | | |
| MBS | 1.2 | | | | | | | | | | |
| BBTS | | 1.1 | 0.85 | 0.85 | | | | | | | |
| MBTS | | | | | 1.2 | | | | | | |
| DPG | | | | 0.25 | 0.40 | 0.60 | | | | | |
| TMTM | | | | | | | | | | | 0.25 |
| TMTD | | | 0.20 | | | | 0.20 | | 0.20 | 0.25 | |
| Accelerator A | | | | | | 1.2 | 1.2 | 1.1 | 1.1 | 1.1 | |
| Part 2 | | | | | | | | | | | |
| Test | | | | | | | | | | | |
| Rheometer (150° C.) | | | | | | | | | | | |
| $t_4$, minutes | 13.4 | 12.0 | 9.0 | 10.9 | 6.7 | 11.7 | 10.5 | 10.7 | 11.9 | 11.0 | 12.7 |
| $t_{90}$, minutes | 30.2 | 28.0 | 18.4 | 25.5 | 20.7 | 28.3 | 30.0 | 31.0 | 34.0 | 30.0 | 31.5 |
| $\Delta$Torque, N.m | 4.88 | 4.81 | 5.13 | 4.47 | 4.96 | 4.71 | 4.86 | 5.39 | 5.22 | 5.40 | 5.34 |
| Mooney Scorch (132° C.) | | | | | | | | | | | |
| $t\Delta 5$, minutes | | | | | | | | 17.4 | 19.6 | 18.4 | 22.1 |
| $t\Delta 3$, minutes | 28.0 | 26.7 | 17.4 | 24.3 | 13.1 | 25.8 | 19.1 | | | | |
| Stress-Strain, cured | | | | | | | | | | | |
| $t_{90}$ minutes at 150° C. | | | | | | | | | | | |
| U.T.S., MPa | 17.6 | 18.4 | 17.5 | 16.4 | 17.8 | 18.0 | 17.0 | 18.6 | 15.8 | 18.6 | 18.4 |
| U.E., % | 570 | 570 | 540 | 580 | 565 | 585 | 530 | 540 | 500 | 555 | 565 |
| 300% M, MPa | 7.4 | 8.0 | 8.2 | 6.6 | 7.8 | 7.7 | 8.0 | 8.5 | 7.9 | 8.2 | 8.0 |

While certain representative embodiments and details have been shown for the purpose of illustrating the invention, it will be apparent to those having skill in this art that various changes and modifications may be made therein without departing from the spirit or scope of the invention.

We claim:

1. A process for the synthesis of 2-(isopropylsulfinyl)-benzothiazole consisting of reacting a 1:1 to 1:3 molar ratio of 2-mercaptobenzothiazole to propylene in a pressure vessel in the presence of a catalytic amount of a monomeric or polymeric arenesulfonic acid optionally in the presence of an inert organic solvent and wherein the reaction is conducted at 125°–200° C. for a period of time sufficient to effect the formation of 2-(isopropylthio)-benzothiazole which is isolated, and thereafter reacting the 2-(isopropylthio)-benzothiazole with up to a 30 percent excess of aqueous sodium hypochlorite under conditions of high frequency mechanical homogenization, at 10°–40° C., in the presence of $NaHSO_4$ or $KHSO_4$ and urea, the amount of $NaHSO_4$ or $KHSO_4$ being sufficient to result in a final pH of the reaction mixture of 1.8–4.0, and the amount of urea being sufficient to suppress the formation of more than 5 weight percent of 2-(isopropylsulfonyl)-benzothiazole in the final product.

* * * * *